United States Patent [19]
Cubbage et al.

[11] Patent Number: 5,652,093
[45] Date of Patent: Jul. 29, 1997

[54] ANALOGUES OF REPORTER GROUPS AS BACKGROUND REDUCERS IN BINDING ASSAYS

[75] Inventors: Michael Lee Cubbage, Houston; Joel Bresser, Bellaire; Mark Blick, Houston; Shyh Chen Ju, Flowermound, all of Tex.

[73] Assignee: Aprogenex, Inc., Houston, Tex.

[21] Appl. No.: 622,514

[22] Filed: Mar. 25, 1996

Related U.S. Application Data

[60] Division of Ser. No. 182,808, Jan. 14, 1994, Pat. No. 5,501,952, which is a continuation-in-part of Ser. No. 916,183, Jul. 17, 1992, abandoned.

[51] Int. Cl.$^6$ .................... C12Q 1/68; C12Q 1/70; G01N 33/53; G01N 33/569
[52] U.S. Cl. .............. 435/5; 435/6; 435/4; 435/7.1; 435/7.2; 435/7.21; 435/7.92; 435/40.5; 435/810; 435/975; 435/962; 436/501; 436/164; 436/172; 935/76; 935/77

[58] Field of Search .................. 435/5, 4, 6, 7.1, 435/7.2, 7.21, 7.72, 7.9, 7.92, 7.93, 40.5, 810, 975, 962; 436/501, 800, 164, 172; 935/76, 77, 78; 530/350, 387.1

[56] References Cited

PUBLICATIONS

Haase, A., In Situ Hybridization: Applications to Neurobiology. Valentino, K.L. et al Editors, (1987), Oxford University Press, New York, New York, pp. 197–219.

Primary Examiner—Carla J. Myers
Attorney, Agent, or Firm—Elman & Associates

[57] ABSTRACT

Assays for target molecules in and from cells and viruses, e.g. nucleic acids, wherein non-specific background is decreased by including an analogue of the reporter group, e.g. a non-fluorescent analogue such as fuchsin, of a fluorescent group such as fluorescein, to decrease non-specific background.

34 Claims, No Drawings

ANALOGUES OF REPORTER GROUPS AS BACKGROUND REDUCERS IN BINDING ASSAYS

This is a division of U.S. patent application Ser. No. 08/182,808 filed Jan. 14, 1994, now U.S. Pat. No. 5,501,952, which is a continuation-in-part of U.S. patent application Ser. No. 07/916,183 filed Jul. 17, 1992, now abandoned.

FIELD OF THE INVENTION

The invention pertains to the reduction of undesired background in hybridization assays for specific molecules in cells and viruses.

BACKGROUND OF THE INVENTION

In an important type of in situ assay, a cell (or virus) is incubated with a target-specific probe carrying a reporter group. If the probe binds to the cell or virus, its presence can be detected by a process designed to detect the reporter group. Reporter groups include fluorescent moieties and moieties that participate in chemiluminescent reactions. Such assays are useful to detect viral nucleic acids, human genes of interest, specific cellular antigens, and other biologically important molecules.

A common limitation on the sensitivity that can be achieved with such assays is that the probes can bind to entities other than the target molecule of interest. Those entities will normally be in the target biological entity (cell or virus), but may also be on the solid support on which the biological entity or purified target molecules are immobilized. The present invention involves incubating the probes with an excess of an analogue of the reporter group, the analogue being sufficiently similar to the reporter group so that it will compete for the non-specific binding sites, but sufficiently different from the reporter group that it will not enter into the reaction used to detect the reporter group. In particular, the invention focuses on reporter groups that comprise an aromatic component.

The present invention involves the discovery of compounds useful as background reducers in in situ assays.

In addition to the general benefit of increased assay sensitivity that the background reducers provide, there is the additional advantage that, for a given level of sensitivity to be reached, cell treatment procedures such as cell fixation need not be as detrimental to cell integrity as would be the case without the use of the background reducers. As a result, the cells retain their structural integrity for a longer time, a consideration particularly important for flow cytometry.

Haase has reported that "Aurintricarboxylic acid ['ATCA'] a potent inhibitor of protein-nucleic acid interactions [R. G. Gonzalez, et al., Biochim. Biophys. Acta 562:534–545, 1979], also improves backpounds [Turtinen and Weitgrefe, unpublished]." Ashley T. Haase, in K. L. Valentino, et al., eds., In Situ Hybridization: Applications to Neurobiology, New York: Oxford University Press, 1987. In accordance with the present invention, applicants regard ATCA as an analogue to FITC. Applicants have surprisingly found that in competition with FITC, ATCA reduces background in their invention, apart from any effect on protein-nucleic acid interactions.

SUMMARY OF THE INVENTION

The invention involves in situ assays in which a compound which is a competitive analogue of a reporter group is added in order to reduce background. A competitive analogue is a substance which binds nonspecifically to a biological entity in competitive equilibrium with the reporter group. A probe that binds to a target molecule is preferably one which binds to that target with high specificity. A reporter group may be a fluorescent dye unattached to a nucleic acid or antibody or other molecule. Preferably, a fluorescent probe is a fluorescent reporter group covalently attached to a nucleic acid molecule, antibody or other molecule capable of binding specifically to a target molecule. In a general aspect, the invention is a detection process or assay capable of detecting a target molecule that may be in or on a biological entity.

In one aspect of the invention, analogues of fluorescent or otherwise luminescent reporter groups are added in order to reduce autofluorescence.

The solutions that contain the analogues, and kits containing materials useful for performing such in situ assays, are also inventions.

The invention is a detection process or assay capable of detecting a target molecule in or on a biological entity (cell or virus). The process emphasizes the steps of:

(1) contacting the biological entity with a solution comprising a probe capable of binding to a target molecule in or on said biological entity, said contacting performed in a manner such that the probe binds to said target molecule so that the probe becomes a target-molecule-bound probe, said probe either comprising a reporter group or comprising means (e.g. enzymatic) for generating a reporter group upon further treatment, (2) contacting the biological entity with a solution comprising a competitive analogue of the reporter group, (3) performing one or more steps that detect the reporter group that is bound to the target molecule but that do not detect the analogue that is bound to the biological entity, wherein step (1) takes place before step (2), after step (2), or during step (2).

Steps (1) and (2) are considered to take place simultaneously ff the probe and the analogue are in the same solution.

Preferably steps (1) and (2) are performed simultaneously by including the probe and the analogue in the same solution.

In a subgeneric aspect of the invention, the reporter group is a fluorescent compound, that is, capable of emitting radiation (visible or invisible) upon stimulation by radiation of a wavelength different from that of the emitted radiation, or through other manners of excitation, e.g. thermal energy transfer. In another subgeneric aspect of the invention, the reporter group is an aromatic compound (having one or more benzene or heteroaromatic rings or polycyclic aromatic or heteroaromatic structures). In another subgeneric aspect of the invention, the reporter group comprises a protein. In a further subgeneric aspect, the reporter group comprises an enzyme. Such an enzyme is desirably capable of catalyzing a reaction that produces a detectable product. Among the conventional detectable products are a radiation-emitting substance (e.g. isoluminol), a fluorescent substance, or a radiation-absorbing substance (e.g. a dye).

In accordance with the present invention, the analogue competes with the reporter group for nonspecific binding sites on the biological entity, effectively blocking the majority of such sites from binding with the reporter group. An excess of the analogue, compared with the reporter group, is desirable because of its effect on endpoint of the competitive equilibrium. This finding is distinguished from the aforementioned statement of Haase, that the effect of ATCA is to inhibit protein-nucleic acid interactions. Also the Gonzalez et al. paper cited by Haase relates to experiments in which the label is radioactive tritium, rather than a reporter group having a particular chemical structure, to which there could be a competitive analogue.

It is preferred that, on a molar basis, the analogue be in excess as regards the reporter group; preferably there should be at least 10 times as much analogue as reporter group.

It is preferred that the ratio by moles of analogue to reporter group be between about 20,000:1 and 100:1. Most desirably the ratio would be between 10,000:1 and 1,000:1.

We have found that for aromatic analogues, the concentration of the analogue in the solution in which treatment with the analogue is carried out may be from about 0.5 mg/ml to about 10 mg/ml. Preferably, the concentration of analogue is between about 1 and 5 mg/ml. Where ATCA is the analogue, this feature distinguishes the present invention from the report of Gonzalez, et al.

Preferred analogues possess most or all of the structural features of the aromatic reporter group. The analogue may additionally have structural features not present in the reporter group or probe.

Preferably, the analogue should be able to permeate a cell or virus. In the case of analogues that are aurin derivatives (rosolic acid derivatives), it is preferred that the analogues have a polar functional group such as a $—CO_2$, $—NH_2$, $—OH$, or $—SO_3$ group, on an aromatic group; examples are chromoxane cyanine R and Chrome Azurol S. A subgroup of preferred analogues are those that block the $—NH_2$ groups on lysines.

Fluorescent reporter groups are detected by allowing the reporter group to absorb a energy and then emit some of the absorbed energy; the emitted energy is then detected.

Chemiluminescent reporter groups are detected by allowing them to enter into a reaction, e.g., an enzymatic reaction, that results in the emission of energy in the form of light.

Other reporter groups, e.g. biotin, may be detected because they can bind to groups such as streptavidin which are bound, directly or indirectly to enzymes, e.g. (alkaline phosphatase or horseradish peroxidase) that can catalyze a detectable reaction. In accordance with another aspect of the present invention, where a fluorescent group is produced by catalysis, competitive analogues of such a fluorescent group are also potentially efficacious at reducing background fluorescence.

To identify compounds that are useful as competitive analogues, compounds are chosen that are considered to be structurally similar to the reporter group of interest. Each candidate analogue is then incubated in a system containing the biological entity in concentrations approximating those of the assay proposed to be performed. One or more steps that detect the reporter group are then performed. The intensity of each signal obtained in this manner is then compared to the signal obtained when the same amount of reporter group is separately incubated with the same amount of biological entity without the addition of the analogue. The competitive analogues that are useful in accordance with the present invention are those compounds wherein the signal detected in the presence of the substance is significantly less than that detected in the absence thereof. A series of such measurements with varying amounts of added analogue can be used to determine the optimal concentration of analogue.

For example, to identify analogues for FITC, a group of compounds having various structural similarities to FITC, was examined. This group consisted of Basic Fuchsin, ATCA, Naphthol Blue Black, Nile Blue, Eosin, and Acid Black 24. These compounds were then tested to determine if they were effective as competitive analogues for FITC in this system by determining the reduction in the mean fluorescence produced by adding varying amounts of each analogue to a hybridization cocktail containing isolated white blood cells (the biological entity in which a proposed assay would be carried out).

A hybridization cocktail was prepared with 2 µg/ml of FITC. For each analogue to be tested, 5 aliquots of 100 µl of the hybridization cocktail were prepared. The first aliquot was left as it was (no added analogue), the second aliquot was brought to 0.05% analogue (wt/vol), the third aliquot was brought to 0.1% analogue, the fourth aliquot was brought to 0.5% analogue, and the fifth aliquot was brought to 1.0% analogue.

Approximately 100,000 white blood cells were suspended in 50 µl of each cocktail to be tested and held at 42° C. for 30 minutes. The reactions were then washed once with Wash solution #1 and a second time with Wash solution #2. The cells were then analyzed on a Coulter Epics flow cytometer.

The results are shown in Example 2. Each of the compounds other than Acid Black 24 created significant reductions (i.e. more than about one-third) in the measured fluorescence at concentrations of about 0.5 mg/ml to 10 mg/ml. Thus each compound other than Acid Black 24 was found to be a competitive analogue of FITC in this system. The most effective of this group were Basic Fuchsin and ATCA.

Fluorescent reporter groups with which this invention can be used include, for example and without limitation: fluorescein (or FITC), Texas Red, coumarin, rhodamine, rhodamine derivatives, phycoerythrin, Perci-P, 4-methylumbelliferyl phosphate, resorufin, and 7-diethylamino coumarin-3-carboxylic acid succinimidyl ester.

Useful reporter groups having near infrared fluorescence include: indocyanine green [CAS 3599-32-4], copper phthalocyanine [CAS 147-14-8].

An example of a useful reporter group having infrared fluorescence is: 3,3'-diethyl-19,11:15,17-dienopentylene-2, 2'-thiapentacarbocyanine.

Chemiluminescent groups with which this invention can be used include isoluminol (4-aminophthalhydrazide). See catalogues of Aldrich Chemical Co. for 1990–91, also Molecular Probes, Inc. catalogue.

In one preferred embodiment of the process, when the reporter group is fluorescein, step (3) comprises measuring light emitted at wavelengths between about 520 nm and 560 nm (especially at about 520 nm), most preferably where the absorption wavelengths of step (3) are less than 520 nm.

A preferred embodiment of the fluorimetric process further comprises a wash step between the steps numbered (2) and (3). A wash step can be performed by centrifuging the cell out of the solution in which it is suspended, then suspending it in a wash solution, and then centrifuging it out of the wash solution. A wash solution is generally a probe-free solution.

In a particular embodiment of the process, the solution that is used in step (2) comprises a probe (comprising a reporter group), an analogue of the reporter group, and a fixative. Such a probe solution is itself an invention.

DETAILED DESCRIPTION OF THE INVENTION

A fluorescent probe that binds to a target molecule is preferably one which binds to that target with high specificity. Such a probe may be a fluorescent dye unattached to a nucleic acid or antibody or other molecule. More preferably, a fluorescent probe is a fluorescent dye covalently attached to a nucleic acid molecule, antibody or other molecule capable of binding specifically to a target molecule. The fluorescent dye may be covalently attached directly to the molecule having target specificity or it may be covalently attached to a linker group, which in turn is covalently attached to the molecule having target specificity. A probe-nucleic acid molecule will be specific for a nucleic acid target molecule with a base sequence complementary to the probe nucleic acid molecule. The probe-nucleic acid molecule hybridizes to the target molecule. A probe-antibody will be specific for a target antigen.

Nucleic acid probes can be used against a variety of nucleic acid targets: viral, prokaryotic, and eukaryotic. The target may be a DNA target such as a gene (e.g., oncogene), control element (e.g., promoter, repressor, or enhancer), or sequence coding for ribosomal RNA, transfer RNA, or RNase P. The target may be RNA such as mRNA, ribosomal RNA, RNase P, tRNA, a viral genome or complementary copy thereof. Additionally, the target may be a "nucleic acid amplification product," i.e., a nucleic acid molecule, either DNA or RNA, which is the result of introducing an enzyme or enzymes into the cell so that such enzymes will make an nucleic acid molecule complementary to one already present in the cell. For example, O. Bagasra et al, *The New England Journal of Medicine*, 326, pp. 1385–1391 (1992), have disclosed the use of the polymerase chain reaction (PCR) with intact cells such that the introduction of polymerase molecules into a cell resulted in additional nucleic acid molecules being formed, each a copy of one previously existing in the cell.

A viral nucleic acid can be part of a virus, in which case the virus may or may not be inside a cell. Alternatively, a viral nucleic acid target may or may not be part of a virus, but may be inside a cell.

Many publications show how to attach a fluorescent dye to a nucleic acid probe or antibody probe.

The cells containing the target molecules may be eukaryotic cells (e.g., human cells), prokaryotic cells (e.g., bacteria), plant cells, or any other type of cell. They can be simple eukaryotes such as yeast or be derived from the more complex eukaryotes such as humans.

The target molecules can be in a non-enveloped virus or an enveloped virus (having an enveloping membrane such as a lipid-protein membrane).

The hybridization assay may be done with fixed cells or (or fixed viruses). Useful precipitation fixatives include ethanol, acetic acid, methanol, acetone, and combinations thereof. Other useful fixatives are known to those skilled in the art. Fixatives, and hybridization of fixed cells, in general, are discussed in PCT international applications WO 90/02173 and WO 90/02204 of Research Development Corp, and U.S. Pat. No. 5,225,326, incorporated by reference herein. Fixatives should provide good preservation of cellular morphology and preservation and accessibility of antigens, and high hybridization efficiency.

The fixative may contain a compound which fixes the cellular components by cross-linking these materials together, for example, paraformaldehyde, glutaraldehyde or formaldehyde. Cross-linking agents, while preserving ultrastructure, often reduce hybridization efficiency; they form networks trapping nucleic acids and antigens and rendering them inaccessible to probes and antibodies. Some also covalently modify nucleic acids preventing later hybrid formation.

The hybridization solution may typically comprise a chaotropic denaturing agent, a buffer, a pore forming agent, a hybrid stabilizing agent.

The chaotropic denaturing agents (Robinson, D. W. and Grant, M. E. (1966) J. Biol. Chem. 241: 4030; Hamaguchi, K. and Geiduscheck, E. P. (1962) J. Am. Chem. Soc. 84: 1329) include formamide, urea, thiocyanate, guanidine, trichloroacetate, tetramethylamine, perchlorate, and sodium iodide. Any buffer which maintains pH at least between 7.0 and 8.0 may be utilized.

The pore forming agent is for instance, a detergent such as Brij 35, Brij 58, sodium dodecyl sulfate, CHAPS™, or Triton X-100. Depending on the location of the target biopolymer, the pore-forming agent is chosen to facilitate probe entry through plasma, or nuclear membranes or cellular compartmental structures. For instance, 0.05% Brij 35 or 0.1% Triton X-100 will permit probe entry through the plasma membrane but not the nuclear membrane. Alternatively, sodium deoxycholate will allow probes to traverse the nuclear membrane. Thus, in order to restrict hybridization to the cytoplasmic biopolymer targets, nuclear membrane pore-forming agents would be avoided. Such selective subcellular localization contributes to the specificity and sensitivity of the assay by eliminating probe hybridization to complementary nuclear sequences when the target biopolymer is located in the cytoplasm. Agents other than detergents such as fixatives may serve this function.

Hybrid stabilizing agents such as salts of mono- and di-valent cations are included in the hybridization solution to promote formation of hydrogen bonds between complementary sequences of the probe and its target biopolymer. Preferably sodium chloride at a concentration from 0.15M to 1M is used. In order to prevent non-specific binding of nucleic acid probes, nucleic acids unrelated to the target biopolymers are added to the hybridization solution.

Many types of solid supports may be utilized to practice the invention. Supports which may be utilized include, but are not limited to, glass, Scotch tape (3M), nylon, Gene Screen Plus (New England Nuclear) and nitrocellulose. Most preferably glass microscope slides are used. The use of these supports and the procedures for depositing specimens thereon will be obvious to those of skill in the art. The choice of support material will depend upon the procedure for visualization of cells or viruses and the quantitation procedure used. Some filter materials are not uniformly thick and, thus, shrinking and swelling during in situ hybridization procedures is not uniform. In addition, some supports which autofluoresce will interfere with the determination of low level fluorescence. Glass microscope slides are most preferable as a solid support since they have high signal-to-noise ratios and can be treated to better retain tissue.

In one embodiment of the process, the target biological entity is immobilized on a solid surface (especially a glass slide where the entity is a cell) during steps (1) through (3). In another embodiment, the target cell or virus is suspended in liquid during the entire process and not immobilized on a solid surface.

The target molecule to which the probe is bound need not be in or on a biological entity. It can be a purified target. A purified target is a molecule, such as a nucleic acid molecule that has been extracted from a cell or a virus, or has been synthesized in a cell-free system. Many procedures have been published for hybridizing a nucleic acid probe against a nucleic acid target that is either in solution or immobilized in single stranded form on a solid support such as a nitrocellulose filter or nylon. The hybridizations vary considerably, depending in part on the level of specificity desired. Some examples are the Southern Blot procedure (*J. Mol. Biol.*, 98, 503–517 (1975)) for electrophoresed and immobilized DNA, the Northern Blot procedure (Seed, B., in *Genetic Engineering: Principles and Methods*, Setlow, J. K. and Hollaender, A., eds., 1982; P. S. Thomas, *Proc. Natl. Acad. Sci. USA*, 77:5201 (1980)) and the use of stringent conditions with short oligomer probes, S. V. Suggs et al, *Proc. Natl. Acad. Sci. USA*, 78, 6613–6617 (1981)).

In another aspect, the invention is a kit which comprises a probe (comprising a reporter group) and an analogue of the reporter group. The probe and the analogue may be combined in a variety of ways. For example, the probe and analogue may (1) be present in the same solution, or (2) be present in separate solutions; alternatively, either the probe or the analogue or both of them may be provided in solid form, so that they must be dissolved in a solvent or solution prior to use.

Exemplary Analogues Useful in the Present Invention

The following compounds are analogues for coumarin [CAS No. 91-64-5], for 4-methylumbelliferyl phosphate [CAS No. 22919-26-2], and for isoluminol (4-aminophthalhydrazide) [CAS No. 3682-14-2]:

1) 8-Hydroxyquinoline-5-sulfonic acid [CAS No. 84-88-8 (anhydrous)],
2) Martius Yellow monohydrate [CAS No. 605-69-6],
3) 5,7-Dichloro-8-Hydroxyquinoline [CAS No. 773-76-2],
4) 1,4,5,8-Naphthalene tetracarboxylic acid [CAS No. 128-97-2],
5) Oxindole [CAS No. 59-48-3],
6) 1,2,3,4-tetrahydro-2-naphthoic acid [CAS No. 53440-12-3],
7) 1,3-Naphthalene disulfonic acid-7-hydroxy.

The following are analogues for indocyanine green [CAS No. 3599-32-4]:

1) Acid Red 40 [CAS No. 12167-45-2],
2) Acid Yellow 42 [CAS No. 6375-55-9],
3) Acid Yellow 40 [CAS No. 6372-96-9],
4) Astrazon Orange G [CAS No. 3056-93-7].

The following are analogues for copper phthalocyanine [CAS No. 147-14-8]:

1) Copper Phthalocyaninetetrasulfonic acid [CAS No. 27360-85-6],
2) Alcian Blue 8GX [CAS No. 33864-99-2]
3) Alcec Blue [a derivative of Alcian Blue].

The following compounds are analogues for carboxytetramethyl rhodamine 5-and-6-succinimidyl ester [CAS No. 75929-56-5] (ex: 550 nm, em: 576 nm):

1) 5- and 6-carboxy-X-rhodamine (ex: 576, em: 597), Available from Molecular Probes, Inc.
2) Xanthene-9-carboxylic acid [CAS No. 82-07-5],
3) Uniblue A Sodium salt (ex: 596, em: 724) [CAS No. 14541-90-3],
4) Thionin (ex:598) [CAS No. 78338-24-4],
5) Eosin-5-isothiocyanate (ex: 522, em: 543) [CAS No. 60520-47-0],
6) α-Conidendrin (Tougalacetone),
7) Eluetherin,
8) Fluorescein (2(3,6-Dihydroxyxanthyl) Benzoic Acid).

The following compounds are analogues for resorufin [CAS No. 635-78-9]:

1) 3,6 Diaminoacridine hydrochloride [CAS No. 952-23-8],
2) Acid Blue 45 [CAS No. 2861-02-1],
3) Acridine Yellow G [CAS No. 135-49-9].

The following compounds are analogues for 7-diethylamino coumarin-3-carboxylic acid succinimidyl ester (ex: 432 nm, em: 472 nm):

1) 7-amino-4-methylcoumarin-3-acetic Acid succinimidyl ester (ex: 351 nm, em: 441 nm),
2) 1,2,3,4-Tetrahydro-1-naphthylamine hydrochloride [CAS No. 49800-23-9],
3) 1,2-dihydroxynaphthalene [CAS No. 574-00-5],
4) 4,8-Dihydroxyquinoline-2-carboxylic Acid [CAS No. 59-00-7],
5) 1,5-dihydroxy-1,2,3,4-Tetrahydronaphthalene [CAS No. 40771-26-4].

The following compounds are analogues for 3,3'-diethyl-19,11:15,17-dienopentylene-2'-thiapentacarbocyanine:

1) Hoechst 33258 [CAS No. 23491-44-3]
2) Congo Red [CAS No. 573-58-0]
3) Direct Blue 71 [CAS No. 4399-55-7]

The following proteins are analogues for alkaline phosphatase (Calf. Intestine), which has a molecular weight of 39 KD:

| | |
|---|---|
| 1) Catalase | 57.5 KD |
| 2) Ovalbumin [CAS 9006-59-1] | 45 KD |
| 3) Aldolase | 40 KD |
| 4) β-Galactosidase | 116 KD |

List of Abbreviations

| Substance | Abbreviation |
|---|---|
| fluorescein isothiocyanate [CAS 3326-32-7] | FITC |
| ethylene diamine tetraacetic acid | EDTA |
| dimethyl sulfoxide | DMSO |
| dithiothreitol | DTT |
| polyvinylpyrrolidone | PVP |
| polyethylene glycol (circa 4000 Mol. Wt.) | PEG 4000 |
| naphthochrome green [CAS 5715-76-4] | Nap Green |
| aurintricarboxylic acid [CAS 4431-00-9] | ATCA |
| standard saline citrate (0.15M NaCl, 0.015M sodium citrate) | SSC |
| disuccinimidylsuberate | DSS |
| phosphate-buffered saline | PBS |

Targets in cells, tissue, and fluids

The hybridization assay can be done for targets in cells in liquid suspension, in cells on slides or other solid supports, and in tissue sections. Such hybridization procedures are known in the art. They are, for example, described in more detail in PCT applications WO 90/02173 and WO 90/02204 and U.S. Pat. No. 5,225,326, incorporated by reference herein.

The target molecules can be in eukaryotic cells or prokaryotic cells. The cells can come from solid tissue (e.g. nerves, muscle, heart, skin, lungs, kidneys, pancreas, spleen, lymph nodes, testes, cervix, and brain) or cells present in membranes lining various tracts, conduits and cavities (such as the gastrointestinal tract, urinary tract, vas deferens, uterine cavity, uterine tube, vagina, respiratory tract, nasal cavity, oral cavity, pharynx, larynx, trachea, bronchi and lungs) or cells in an organism's fluids (e.g., urine, stomach fluid, sputum, blood and lymph fluid) or stool.

Flow cytometry

A Coulter Profile II flow cytometer can be used.

For experiments with FITC as the probe dye, the dye is first excited with light of 488 nm and then the emitted light is measured. For the emitted light (for LFL1), a 540 bp (40) filter was used; i.e., only light with a wavelength between 520 nm and 560 nm is allowed to pass. The filter for LFL3 is a 635 long pass filter; i.e., it allows any light over 635 nm wavelength to pass.

Solutions

Fixation solution F has the following ingredients: 4 volumes ethanol, 5 volumes of 1× PBS, 1 volume of glacial acetic acid.

Hybridization cocktail HC has the following inkedients; 5× SSC (0.75M NaCl, 0.075M sodium citrate); 30% Formamide (v/v); 3% Triton X-100 (v/v); 0.4M Guanidine isothiocyanate; 0.16M sodium phosphate buffer (pH 6); 15× Ficoll/PVP (polysucrose 400,000 mol wt/polyvinylpyrrolidone); 1 mg/ml Sheared Salmon Sperm DNA; 10 mM EDTA; 25 mM DTT; 5% PEG 4000. In the foregoing, 500× Ficoll/PVP is 5 g of Ficoll type 400 (polysucrose 400,00 mol wt) plus 5 g of PVP (polyvinylpyrrolidone) dissolved in water to a total volume of 100 ml; 15× Ficoll/PVP indicates that 500× Ficoll/PVP has been diluted by a factor of 15/500 with water.

Ficoll (Pharmacia) is a nonionic synthetic polymer of sucrose.

If an analogue is added to the cocktail, its preferred concentration is from 0.01 to 0.5% w/v.

For hybridization cocktails used with a nucleic acid probe, the temperature for the hybridization reaction preferably between 30° C. and 46° C.; the time preferably is between 5 minutes and 16 hours.

Wash solution #1 has the following composition: 0.4M guanidine isothiocyanate; 0.1% Triton X-100 (an alcohol derivative of polyoxyethylene ether, see Aldrich Chemical Co. catalogue for 1990–91; 0.1% v/v); 0.1× SSC; in deionized water.

Wash solution #2 has the following composition: 0.1% Triton X-100 (v/v); 0.1× SSC; in deionized water.

1× SSC has the following composition: 0.15M NaCl, 0.15M sodium citrate, pH 7.0. 2× SSC is composed so that upon a 1:1 dilution with water, SSC would be produced; 10× SSC is composed so that upon a 1:10 dilution with water, SSC would be produced.

1× PBS is phosphate-buffered saline and had the formula, 0.136M NaCl, 0.003M KCl, 0.008M $Na_2HPO_4 \cdot 7H_2O$, 0.001M $KH_2PO_4$.

If a dye-labeled antibody is used as the probe, then the probe may be dissolved in PBS, possibly supplemented with bovine serum albumin (BSA) while it is allowed to react with target cells preferably at a temperature in the range 4° C. to 34° C. The cells need not be fixed (e.g. when the antibody target is a cell-surface antigen), or may be fixed after the probe-target incubation is completed, or may be fixed prior or during the probe-target incubation. The analogue of the probe's reporter group is preferably present while the probe is being mixed with the target cells or virus.

Additional useful reagents and solutions

Useful reagents and solutions for executing the inventions described herein include 0.0025% Evans Blue and/or 10% dodecyl alcohol in the solution analyzed cytofluorimetrically; 5% Vitamin E in the hybridization cocktail used where the assay target is in a biological entity; about 8% DMSO (v/v) with about 5% or 10% squalane and about 5% or 10% pyrrolidinone in the hybridization cocktail when the target is in a biological entity; 5 µl of DTT and 5 µl of Proteinase K (1 mg/ml) solution are added to 100 µl of cocktail and the hybridization reaction is run, for example, at 42° C. for 5 min, then at 95° C. for 5 min, and then at 42° C. for 2 min, when the target is in a biological entity.

Where 30-mers are used, probes against both strands of a double-stranded target can be used, provided that the probes are "out-of phase" along the map of the target so that any probe is not complementary in base sequence to more than about 15 nucleotides of a probe to the other strand of the target. In that way, probes hybridize to the target and not to each other. If the probes are labelled at both the 3' and 5' ends with an aminohexyl linker, and tetraethyl rhodamine is the dye attached to each linker, it is preferred to use 25-mers and space the targets along a given strand by five base pairs; and if both strands of a target are hybridized to, the end-over-end overlap of probes to opposite strands can be about 10 bases.

Cell lines used in the Examples

H9 cells are a human-derived lymphoma cell line.

Reagents

Reagents can be purchased from any of a variety of sources including Aldrich Chemical Co., Milwaukee, Wis.; Sigma Chemical Co., St. Louis, Mo.; Molecular Probes, Inc., Eugene, Ore.; Clontech, Palo Alto, Calif.; Kodak, Rochester, N.Y.; and Spectrum Chemical Manufacturing Corp., Gardena, Calif.

EXAMPLES

Example 1

Preparation of Cells

The H9 cell line was used in the following experiment. Cultured cells were washed with nuclease-free Phosphate Buffered Saline (PBS) and placed in a single cell suspension at a concentration that resulted in clearly separated cells. The cells were spun down to a pellet and the supernatant drained off. The cells were resuspended in 40% ethanol, 50% PBS, and 10% glacial acetic acid and left for 12–16 hours at 4° C. After fixation, the cells were spun to remove the fixative and then washed once in 1× PBS and resuspended in 2× SSC. (The cells should be used immediately.)

H9– cells were uninfected with human immunodeficiency virus (HIV)

H9+ cells had one copy of HIV strain BH102 integrated in DNA form.

Preparation of Probes

The HIV sequences used as probes were accessed via GenBank, version 69.0, and prepared (See Table A). The negative probe, NR was derived from the nitrogen reductase gene found in bacteria and known not to hybridize to nucleic acid within eukaryotic cells. The cells were 39-bases in length.

TABLE A

| Probe Destination | GenBank Locus | Fluorescent Label | Name |
|---|---|---|---|
| HIV | HUMB102 | fluorescein | |

Probe Synthesis & Labeling

The above-mentioned sequences are divided into several 25-base oligonucleotides and synthesized using DNA synthesizers (Applied Biosystem DNA Synthesizer, Model 380B) and using the recommended ABI reagents. The oligonucleotides were then coupled to at their 5' end to FITC, a fluorescent dye (Molecular Probes, FITC) and purified by column chromatography and HPLC. Coupling was through an aminohexyl moiety, Aminolink (Applied Biosystems, Inc.)

Hybridization

For the hybridization procedure, to pelleted cells were added 50 µl of a hybridization cocktail consisting of 30% formamide, 5× SSC, 0.16M sodium phosphate buffer, pH 7.4, 1 µg/µl sheared DNA, 3% (v/v) Triton X-100, 5% PEG 4000, 25 mm DTT, 0.4M guanidine isothiocyanate, 15×

Ficoll/PVP, and the probe was added at a concentration of 2.5 µg/ml. Hybridizations were carded out at 42° C. for 30 minutes.

Additionally, as specified below, either 0.05% ATCA, 0.1% ATCA, 0.05% Nap Green or 0.1% Nap Green was added to the cocktail.

Washing

Proper washing after the hybridization reaction is essential to minimize background due to non-specific binding of probe. Post-hybridization the cells were placed in a 15 ml conical tube to which was added 10 ml of a wash solution, consisting of 0.1× SSC, 0.4M guanidine isothiocyanate, and 0.1% Triton X-100 at a temperature of 42° C. The solution was agitated until the cells were a single cell suspension and then spun at 250× g for 5 minutes. The supernatant was removed and to the pellet was added 10 ml of a wash solution, consisting of 0.1× SSC, 0.1% Triton at a temperature of 42° C. The solution was agitated until the cells were a single cell suspension. The cells were spun at 250×g for 5 minutes. The supernatant was removed and the cell pellet resuspended in 0.2 ml counterstain solution consisting of 0.0025% Evans Blue in 1× PBS.

Flow Cytometer Use and Interpretation

The cells were analyzed on a Profile II™ made by Coulter Instruments. The instrument uses a 488 nm argon laser, a 525 nm band pass filter for FL1 and a 635 nm band pass filter for the counterstain. For each sample analyzed the sample containing the negative probe is analyzed first and the quad-stats are set so that less than 0.01% of the cells fall in the upper-right quadrant or lower-right quandrant. Next the sample analyzed with the HIV probes is analyzed under exactly the same parameters as the sample analyzed with the negative probe. Since the quad-stats have been previously set and the two samples have been handled identically, any number of cells (above 0.01%) that are recorded in the upper right quadrant are scored as positive.

Results

Tables B and C show results obtained with a FITC-labeled DNA probe specific for HIV sequences in H9– (uninfected) and H9+ (HIV infected) cells. In Table C, the results were obtained with and without Evans Blue in the solution containing the cells during flow cytometry.

TABLE B

| Cocktail | H9– | H9+ |
|---|---|---|
| flow | 12 | 226 |
| 0.05% NG | 11 | 232 |
| 0.05% ATCA | 8 | 216 |

TABLE C

| | No Evans Blue | | Evans Blue | |
|---|---|---|---|---|
| Cocktail | H9– | H9+ | H9– | H9+ |
| flow | 18.9 | 189 | 0.127 | 128 |
| 0.1% NG | 19.7 | 226 | 0.133 | 145 |
| 0.1% ATCA | 12.4 | 210 | 0.125 | 146 |
| 1% NG | 19.1 | 213 | 0.133 | 146 |
| 1% ATCA | 20.3 | 137 | 0.212 | 121 |

The results show ATCA was effective for reducing background at concentrations of 0.05% and 0.1%. The results also show increased signal when naphthochrome green and ATCA were used, with Evans Blue present during flow cytometry.

Example 2

Competition with Free FITC as a Function of Analogue Concentration

Example 2 exemplifies a test to determine if a compound is a competitive analogue to a reporter group. Here, the reporter group is FITC, and the biological entity is white blood cells. The results of Example 2 also show that ATCA can function as a competitive analogue within the scope of the present invention.

Isolated white blood cells (WBC) were fixed in 0.5% paraformaldehyde (PF) for 12 hours at 4° C. and then washed in 2× SSC to remove any remaining PF. Approximately 100,000 cells were transferred to a 1.5 ml tube for each cocktail to be tested. The cells were spun for 1 minute at 200×g to pellet the cells and the supernatant was aspirated.

The hybridization cocktail (HC) had the following ingredients:

5× SSC (0.75M NACl, 0.075M sodium citrate); 30% Formamide (v/v); 3% Triton X-100 (v/v) (Triton X-100 is an alcohol derivative of polyoxyethylene ether, see Aldrich Chemical Co. catalogue for 1990–91); 0.4M Guanidine isothiocyanate; 0.16M sodium phosphate buffer (pH 6); 15× Ficoll/PVP (polysucrose 400,000 mol wt/polyvinyl pyrrolidone); 1 mg/ml Sheared Salmon Sperm DNA; 10 mM EDTA; 25 mM DTT; 5% PEG 4000. In the foregoing, 500× Ficoll/PVP is 5 g of Ficoll type 400 (polysucrose 400,00 mol wt) plus 5 g of PVP (polyvinylpyrrolidone) dissolved in water to a total volume of 100 ml; 15× Ficoll/PVP indicates that 500× Ficoll/PVP has been diluted by a factor of 15/500 with water. Ficoll (Pharmacia) is a nonionic synthetic polymer of sucrose. A stock solution of 0.1 mg/ml FITC in dimethylformamide was prepared. It was added to the HC in a quantity to produce a final concentration of FITC in the HC of 2 µg/ml.

For each of the following analogues to FITC, namely: Acid Black 24 [CAS 3071-73-6], Basic Fuchsin [CAS 569-61-9], Eosin [CAS 548-24-3], Naphthol Blue Black [CAS 1064-48-8], Nile Blue [CAS 2381-85-3], and ATCA [CAS 4431-00-9] the cocktails were prepared as follows:

A series of 100 µl aliquots of HC was prepared and labeled A–E. The A aliquots were left as they were (no analogue was added), the B aliquots were brought to 0.05% analogue (wt/vol), the C aliquots were brought to 0.1% analogue (wt/vol), the D aliquots were brought to 0.5% analogue (wt/vol), and the E aliquots were brought to 1.0% analogue (wt/vol).

After each cell pellet was resuspended in the cocktail, they were held at 42° C. for 30 minutes. The reactions were then diluted with 1 ml of Wash solution #1 which was preheated to 42° C. Wash solution #1 had the following composition: 0.4M guanidine isothiocyanate; 0.1% Triton X-100 (v/v); 0.1× SSC; in deionized water.

The cells were then pelleted at 200×g for 2 minutes.

The supernatant was aspirate& and the cell pellet was resuspended in 1 ml of Wash solution #2 which had been preheated to 42° C. Wash solution #2 had the following composition: 0.1% Triton X-100 (v/v); 0.1× SSC; in deionized water.

The cells were pelleted at 200×g for 2 minutes. The supernatant was aspirated and the cell pellet was resuspended in 0.5 ml of 1× PBS. The cells were then analyzed on a Coulter Epics II flow cytometer, gating on fluorescent channel 1 (band pass filter to allow light between 510 nm and 530 nm). In the tables below, 100% fluorescence is the amount measured in the solution to which no analogue had been added. In each instance, the concentration of FITC was 2 µg/ml. Of the compounds tested, only Acid Black 24 failed to provide at least a one-third (33⅓%) reduction of background fluorescence under the conditions of the test.

TABLE D

| | Basic Fuchsin | |
|---|---|---|
| Concentration (mg/ml) | Concentration (×10⁻⁵M/ml) | % Mean Fluorescence |
| 0.00 | 0.00 | 100 |
| 0.50 | 0.15 | 23 |
| 1.00 | 0.31 | 1 |
| 5.00 | 1.54 | 0 |
| 10.0 | 3.09 | 0 |

TABLE E

| | ATCA | |
|---|---|---|
| Concentration (mg/mL) | Concentration (×10⁻⁵M/mL) | % Mean Fluorescence |
| 0.00 | 0.00 | 100 |
| 0.50 | 0.12 | 71 |
| 1.00 | 0.24 | 60 |
| 5.00 | 1.18 | 20 |
| 10.0 | 2.37 | 4 |

TABLE F

| | Naphthol Blue Black | |
|---|---|---|
| Concentration (mg/ml) | Concentration (×10⁻⁵M/ml) | % Mean Fluorescence |
| 0.00 | 0.00 | 100 |
| 0.50 | 0.08 | 87 |
| 1.00 | 0.16 | 71 |
| 5.00 | 0.81 | 13 |
| 10.0 | 1.62 | 14 |

TABLE G

| | Nile Blue | |
|---|---|---|
| Concentration (mg/ml) | Concentration (×10⁻⁵M/ml) | % Mean Fluorescence |
| 0.00 | 0.00 | 100 |
| 0.50 | 0.14 | 64 |
| 1.00 | 0.28 | 33 |
| 5.00 | 1.41 | 33 |
| 10.0 | 2.83 | 27 |

TABLE H

| | Eosin | |
|---|---|---|
| Concentration (mg/ml) | Concentration (×10⁻⁵M/ml) | % Mean Fluorescence |
| 0.00 | 0.00 | 100 |
| 0.50 | 0.08 | 75 |
| 1.00 | 0.16 | 75 |
| 5.00 | 0.80 | 70 |
| 10.0 | 1.60 | 60 |

TABLE I

| | Acid Black 24 | |
|---|---|---|
| Concentration (mg/ml) | Concentration (×10⁻⁵M/ml) | % Mean Fluorescence |
| 0.00 | 0.00 | 100 |
| 0.50 | 0.07 | 73 |
| 1.00 | 0.14 | 77 |
| 5.00 | 0.68 | 81 |
| 10.0 | 1.37 | 75 |

The data demonstrate that the analogues lower the background fluorescence in the white blood cell biological entity in the presence of FITC. Thus the effect discovered by the inventors is separate from any effect that ATCA might have on nucleic acid-protein binding.

Example 3

Protein Analogue with Enzyme-Labelled Probe

Enzyme-linked probes may be used to detect specific molecules in cells or tissues. In these enzyme immunoassays, a probe can be linked directly to an enzyme that will specifically bind to the target molecule. Alternatively, amplification processes can be employed, whereby a primary enzyme (which is not labelled with a probe) is reacted with the target molecule. A secondary probe-labelled enzyme is then used to detect the first antigen-antibody complex by binding to the antibody. When alkaline phosphatase and a chemiluminescent probe are used, the antigen-antibody complexes may be observed as dark bands or spots on X-ray film.

A nucleic acid probe is linked to alkaline phosphatase as follows:

Oligonucleotides are synthesized on a DNA Synthesizer (e.g., Applied Biosystems DNA Synthesizer Model 380 B using the recommended A.B.I. reagents) and in the last stage an aminohexyl phosphate linker is attached to the 5' end. 50 µg, 5.795 nmole, of the 5'-aminohexyl oligodeoxynucleotides is dissolved in 12.41 µl of linker buffer, consisting of 100 mM sodium borate, 2 mM EDTA pH 8.25. To this is added 24.83 µl (674.85 nmole) of DSS in DMSO solution (10 mg/ml). This solution is vigorously vortexed and allowed to stand at room temperature in the dark. After 15 min, 0.42 ml of 1-butanol is added slowly. The mixture is then subjected to vigorous vortexing at low speed and centrifuged for one minute in a microcentrifuge (15,000 rpm). 1-Butanol is carefully removed with a pipet. The precipitate is extracted two more times with 1-butanol (0.42 ml). The sample is then cooled in dry ice. The remaining amount of 1-butanol is removed by lyophilization. When the sample is dry, (about 15 min), 42 µl (300 µg) of alkaline phosphatase (Boehringer Mannheim, Indianapolis, Ind., cat no. 1097-075)(concentration: 7.2 mg/ml) is added. The tube is gently tapped several times to dissolve the solid. The sample is placed in the dark on a gyrator for 16 hr (T=23.2° C., rpm=130). The next day the probe is purified by Waters HPLC using a baseline 810 chromatography work station.

For the hybridization procedure, to pelleted cells are added 50 µl of a hybridization cocktail consisting of 30% formamide, 5× SSC, 0.16M sodium phosphate buffer, pH 7.4, 1 µg/µl sheared DNA, 3% (v/v) Triton X-100, 5% PEG 4000, 25 mM DTT, 0.4M guanidine isothiocyanate, 15× Ficol/PVP, and the probe was added at a concentration of 2.5 µg/ml. Hybridizations are carried out at 42° C. for 30 minutes. Additionally, the analogue would be added to the cocktail, at a concentration of 0.5 mg/ml to 100 mg/ml. The analogue may be, for example, ovalbumin, catalase, aldolase, or β-Galactosidase.

After the cells have hybridized to the probe and have been washed, the cells are suspended in 0.25 ml of substrate solution. The substrate solution consists of AttoPhos (or 4-MUP) in 2.4M diethylanolamine, 0.057 nM $MgCl_2$, 0.005% $NAN_3$ pH 10.0. The cells are incubated for 10 min at about 23° C. and then analyzed on a flow cytometer. Cells are run on a flow cytometer and histograms are generated which display the staining dye fluorescence in one axis (LFL2 or LFL3) and the probe fluorescence on the other axis (LFL1).

A "Count vs. LFL1" histogram is generated. ("Count" refers to cell count.) This histogram may be used as the basis for determining whether the compound tested is an effective competitive analogue. Additional histograms and an FS/SS plot may also be generated.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Having thus described the invention, what is desired to protect by Letters Patent and hereby claimed is:

1. A detection process, which process comprises the steps of:
   (1) contacting a biological entity with a solution comprising a probe associated with a reporter group, wherein said probe is a protein moiety capable of binding to a target molecule in or on said biological entity, said contacting being performed in a manner such that said probe binds to said target molecule so as to make said probe a target-molecule-bound probe;
   (2) incubating the biological entity with a solution comprising a competitive analogue of said reporter group, said competitive analogue being a substance that binds nonspecifically with said biological entity in competitive equilibrium with said reporter group and wherein said competitive analogue is not bound to be a probe;
   (3) performing one or more steps that will detect said reporter group associated with said probe bound to the biological entity but that will not detect a competitive analogue bound to the biological entity;
   wherein step (1) takes place before step (2), after step (2), or during step (2);
   wherein said competitive analogue is a substance other than aurintricarboxylic acid.

2. A process of claim 1 wherein wherein said biological entity is a cell or a virus.

3. A process of claim 1 wherein said probe is selected from the group consisting of an antibody, a lectin, a specific binding protein, avidin and streptavidin.

4. A process of claim 3 wherein said probe is an antibody capable of binding to a target antigen in or on the biological entity.

5. A process of claim 1 wherein steps (1) and (2) are performed simultaneously by including the probe and the competitive analogue in the same solution.

6. A process of claim 1 which further comprises a wash step between the steps numbered (2) and (3), said wash step comprising washing the biological entity in a probe-free solution.

7. A process of claim 1 wherein prior to step (1) the biological entity has been treated with a fixative.

8. A process of claim 1 wherein said contacting is performed on said biological entity wherein said biological entity is suspended in liquid.

9. A process of claim 1 wherein said contacting is performed on said biological entity wherein said biological entity is immobilized on a solid support.

10. A process of claim 1 wherein the reporter group is an aromatic compound.

11. A process of claim 1 wherein the reporter group is a fluorescent moiety and step (3) comprises detecting said reporter group by a fluorimetric detection process.

12. A process of claim 11 wherein the reporter group is selected from the group consising of fluorescein, Texas Red, coumarin, rhodamine, carboxytetramethyl rhodamine 5- and 6-succinimidyl ester, phycoerythrin, Perci-P, 4-methylumbelliferyl phosphate, resorufin, copper phthalocyanine, 7-diethylamino coumarin-3-carboxylic acid succinimidyl ester, indocyanine green, 3,3'-diethyl-19, 11:15,17-dienopentylene-2,2'-thiapentacarbocyanine, 4-aminophthalhydrazide, and derivatives of the aforementioned compounds.

13. A process of claim 12 wherein the reporter group is fluorescein or a derivative thereof and wherein step (3) comprises irradiating said reporter group at wavelengths of less than 520 nm and measuring light emitted at wavelengths between about 520 nm and 560 nm.

14. A process of claim 12 wherein the reporter group is fluorescein, rhodamine or a derivative of fluorescein or rhodamine, and the competitive analogue is aurin or a derivative thereof other than aurintricarboxylic acid.

15. A process of claim 1 wherein the reporter group is a chemiluminescent moiety and step (3) comprises detecting said reporter group by a chemiluminescent detection process.

16. A process of claim 15 wherein the reporter group is isoluminol.

17. A process of claim 1 wherein the reporter group is an enzyme and step (3) comprises detecting said reporter group by an enzymatic detection process.

18. A process of claim 17 wherein the reporter group is alkaline phosphatase or horseradish peroxidase.

19. A process of claim 18 wherein the reporter group is alkaline phosphatase and the competitive analogue is Catalase or Ovalbumin or Aldolase or β-Galactosidase.

20. A process of claim 1 wherein the reporter group is coumarin or 4-methylumbelliferyl phosphate or 4-aminophthalhydrazide and the competitive analogue is 8-hydroxyquinoline-5-sulfonic acid or Martius Yellow monohydrate or 5,7-dichloro-8-hydroxyquinoline or 1,4,5, 8-naphthalene tetracarboxylic acid or Oxindole or 1,2,3,4-tetrahydro-2-naphthoic acid or 1,3-(7-hydroxynaphthalene) disulfonic acid.

21. A process of claim 1 wherein the reporter group is indocyanine green and the competitive analogue is Acid Red 40 or Acid Yellow 42 or Acid Yellow 40 or Astrazon Orange G.

22. A process of claim 1 wherein the reporter group is copper phthalocyanine and the competitive analogue is Copper Phthalocyaninetetrasulfonic acid or Alcian Blue 8GX or Alcec Blue.

23. A process of claim 1 wherein the reporter group is carboxytetramethyl rhodamine 5- and 6-succinimidyl ester and the competitive analogue is 5-carboxy-X-rhodamine or 6-carboxy-X-rhodamine or xanthene-9-carboxylic acid or Uniblue A Sodium salt or Thionin or Eosin-5-isothiocyanate or α-Conidendrin or Eluetherin or Fluorescein.

24. A process of claim 1 wherein the reporter group is resorufin and the competitive analogue is 3,6-diaminoacridine hydrochloride or Acid Blue 45 or Acridine Yellow G.

25. A process of claim 1 wherein the reporter group is 7-diethylamino coumarin-3-carboxylic acid succinimidyl ester and the competitive analogue is 7-amino-4-methylcoumarin-3-acetic acid succinimidyl ester or 1,2,3,4-tetrahydro-1-naphthylamine hydrochloride or 1,2-dihydroxynaphthalene or 4,8-dihydroxyquinoline-2-carboxylic acid or 1,5-dihydroxy-1,2,3,4-tetrahydronaphthalene.

26. A process of claim 1 wherein the reporter group is 3,3'-diethyl-19,11:15,17-dienopentylene-2,2'-thiapentacarbocyanine and the competitive analogue is Hoechst 33258 or Congo Red or Direct Blue 71.

27. A process of claim 1 wherein the biological entity is human biological material or a human cell.

28. A detection process, which process comprises the steps of:

(1) contacting a biological entity with a solution comprising a probe associated with a fluorescent reporter group, which probe is a protein moiety capable of binding to a target molecule in or on said biological entity, said contacting performed in a manner such that the probe binds to said target molecule so as to make that probe a target-molecule-bound probe;

(2) incubating the biological entity with a solution comprising a competitive analogue of said fluorescent reporter group, said competitive analogue being at a concentration of at least 0.5 mg/ml, and said competitive analogue being a substance other than aurintricarboxylic acid and wherein said competitive analogue is not bound to a probe;

(3) performing one or more steps that will detect said fluorescent reporter group associated with said probe bound to the biological entity but that will not detect a competitive analogue bound to the biological entity;

wherein step (1) takes place before step (2), after step (2), or during step (2).

29. A process of claim 28 wherein said biological entity is a cell or a virus.

30. A process of claim 28 wherein the competitive analogue is aurintricarboxylic acid.

31. A process of claim 30 wherein step (2) takes place during step (1).

32. A process of claim 31 wherein the ratio by moles of competitive analogue to reporter group is between about 20,000:1 and 100:1.

33. A solution for use in a detection process that comprises the following:

1) a probe that comprises a reporter group and a protein moiety associated therewith selected from the group consisting of an antibody, a lectin, a specific binding protein, avidin and streptavidin; and 2) a competitive analogue of said reporter group wherein said competitive analogue is not bound to a probe.

34. A kit for use in a detection process that comprises the following:

1) a probe that comprises a reporter group and a protein moiety associated therewith selected from the group consisting of an antibody, a lectin, a specific binding protein, avidin and streptavidin; and 2) a competitive analogue of said reporter group wherein said competitive analogue is not bound to a probe.

* * * * *